(12) United States Patent
Frisch

(10) Patent No.: US 6,706,521 B2
(45) Date of Patent: Mar. 16, 2004

(54) BED CLEANING SYSTEM FOR FLUIDIZED-BED BIOREACTORS

(75) Inventor: Samuel Frisch, Manalapan, NJ (US)

(73) Assignee: Envirogen, Inc., Lawrenceville, NJ (US)

(*) Notice: Subject to any disclaimer, the term of this patent is extended or adjusted under 35 U.S.C. 154(b) by 284 days.

(21) Appl. No.: 09/930,894

(22) Filed: Aug. 16, 2001

(65) Prior Publication Data

US 2003/0036191 A1 Feb. 20, 2003

(51) Int. Cl.⁷ .............................................. C12M 1/14
(52) U.S. Cl. ........................... 435/299.1; 435/308.1; 210/618; 210/792; 210/151; 210/270
(58) Field of Search ..................... 435/299.1, 308.1; 210/617, 618, 792, 150, 151, 189, 274, 269, 270

(56) References Cited

U.S. PATENT DOCUMENTS

| | | | | | |
|---|---|---|---|---|---|
| 4,177,144 A | * | 12/1979 | Hickey et al. | ................ | 210/86 |
| 4,545,909 A | * | 10/1985 | Atkinson et al. | ........... | 210/618 |
| 4,892,818 A | * | 1/1990 | Ramp | ........................... | 435/30 |
| 4,904,600 A | * | 2/1990 | Ramp | ...................... | 435/293.1 |
| 5,487,829 A | * | 1/1996 | Safferman et al. | .......... | 210/151 |
| 5,750,028 A | * | 5/1998 | Frisch | ........................ | 210/618 |
| 5,788,842 A | * | 8/1998 | Frisch | ........................ | 210/618 |
| 5,985,149 A | * | 11/1999 | Raetz et al. | ................ | 210/617 |

* cited by examiner

Primary Examiner—David A. Redding
(74) Attorney, Agent, or Firm—RatnerPrestia

(57) ABSTRACT

A reaction chamber is adapted to contain a fluidized bed having a slurry of liquid, media and biomass. A lift and motive fluid are provided to urge slurry from the reaction chamber through a passage from a slurry inlet to a slurry discharge. The height of the slurry inlet is adjustable with respect to the bottom of the reaction chamber to help control the fluidized bed.

18 Claims, 6 Drawing Sheets

BED CLEANING SYSTEM FOR FLUIDIZED-BED BIOREACTORS

TECHNICAL FIELD

The present invention relates to a fluidized-bed bioreactor, particularly to a bioreactor for separating contaminants from liquids and degrading the separated contaminants.

BACKGROUND OF THE INVENTION

Conventional fluidized-bed bioreactors suffer from operational drawbacks in that the media or carriers of the fluidized bed may be subject to excessive buildup of biologically active materials (or "biomass") and precipitates, thereby causing compromised flow distribution, excessive media and/or biomass carryover, crusting, increased clogging and the like. Specifically, if not properly limited, biomass and precipitate buildup causes uncontrolled bed expansion in the bioreactor, which is detrimental to system performance. Uncontrolled media bed expansion in a fluidized bed biological reactor can also result in an undesirable loss of media.

Media bed expansion can, under certain circumstances, be limited by the application of shear toward the top of the fluidized bed, but the success of such a control strategy depends upon whether excess biomass and suspended solids can be transported to the top of the fluidized bed. More specifically, it is recognized that such transportation of excess biomass and suspended solids toward the top of the bed is promoted by several dominant mechanisms. For example, media grains that are coated with thicker layers of biomass tend to have an overall particle density that is less than the average particle density within the fluidized bed. Those particles, therefore, are transported to the top of the fluidized bed by virtue of upward moving fluid flow as well as the reduced particle density. Also, the movement of media particles within the fluidized bed tends to cause shear to help dislodge biomass from the surface of the media particles. That sheared biomass is then transported in an upward direction as it is carried by the bulk fluid flow.

Nevertheless, several conditions tend to limit the ability to apply shear at the top of a fluidized bed. For example, shear-resistant biological growth can limit the effect of shear at the top of the fluidized bed reactor, especially when conditions within the fluidized bed reactor result in a rapid growth of filamentous organisms or "blooms". Under such conditions, the transport of media particles with thick biomass coatings is inhibited, and excessive biomass accumulation can occur in the lower and central regions of the fluidized bed. Excessive bed growth can therefore result, as the shear applied at the top of the fluidized bed does not impact the lower and central regions of the bed adequately.

Also, the impact of shear at the top of the fluidized bed reactor can be compromised if a shear-resistant or high-density precipitate (e.g., an inorganic film) forms within the fluidized bed. Such precipitate can accumulate throughout the fluidized bed, thereby encouraging uncontrolled bed growth. For example, iron hydroxide may be precipitated if ferrous iron is oxidized under aerobic conditions.

Attempts have been made in the past to overcome this long-standing problem of uncontrolled bed growth. The operation of the fluidized bed reactor can be interrupted periodically in order to conduct chemical treatment of the media bed. For example, acid washing of the media can be conducted in order to remove iron precipitate, and shock treatment can be conducted with sodium hypochlorite. The operation of the fluidized reactor can also be interrupted periodically to transfer the media to a holding tank for later return to the fluidized bed reactor. Shear is thereby imparted in each of these transfer operations so as to loosen attached solids from the media. Such loosening of the solids from the media by media transfer can be enhanced by external washing or chemical treatment. Finally, the replacement rates of the media can be elevated in order to replenish the media that tends to be lost as a result of uncontrolled bed expansion.

U.S. Pat. Nos. 4,892,818 and 4,904,600, both to Floyd Ramp, describe a fluidized bed bioreactor with recirculating wash liquid. Wash liquid is forced from the bioreactor to a separator for contaminant removal. The wash liquid is recycled into the bioreactor by a pump. A retaining screen provided at the wash liquid outlet prevents circulation of the packing material.

U.S. Pat. No. 4,545,909, issued to Bernard Atkinson et al., describes a bioreactor for treating sewage. Media and the attendant water and biomass is delivered to a straining device, separated from the water, and transported to a machine that separates biomass. The separation machine separates biomass by compression, intense vibration, or other mechanical methods. Alternatively, a chemical or biological separation method, such as extended aeration, is used.

It has been found that application of conventional techniques to remove excess biomass from the slurry of biomass, water and media are sometimes insufficient to help (1) overcome bed expansion caused by shear resistant biological growth and (2) reduce the formation of precipitates formed by the microorganisms found in oxygen deficient zones of bioreactors. Thus, there remains a need in the industry for an improved system for separating accumulated biomass from a slurry of a fluidized-bed bioreactor to inhibit uncontrolled bed expansion and precipitate accumulation.

It is therefore an object of the invention to provide a system for controlling bed expansion. Other objects and advantages of the invention will become apparent to those skilled in the art from the drawings, the detailed description of preferred embodiments, and the appended claims.

SUMMARY OF THE INVENTION

One aspect of the invention provides a reaction chamber adapted to contain a fluidized bed having a slurry of liquid, media and biomass. A lift and motive fluid are provided to urge slurry from the reaction chamber through a passage from a slurry inlet to a slurry discharge. The height of the slurry inlet is preferably adjustable with respect to the bottom of the reaction chamber.

In another embodiment, the lift urges the slurry from the bioreactor through a passage from the slurry inlet to a biomass separator. The excess biomass is preferably removed via a biomass discharge and the slurry, with a reduced concentration of biomass, is preferably returned to the bioreactor.

In yet another embodiment, a portion of the slurry that exits the biomass separator is preferably used as part or all of the motive fluid that urges additional slurry through the passage from the slurry inlet to the biomass separator.

In operation, preferably by adjustably positioning the slurry inlet at a height above the bottom of the reaction chamber, a portion of the slurry in the fluidized bed is urged from the fluidized bed through the passage. Optionally, excess biomass is separated from the slurry and the slurry is then discharged through a slurry discharge and returned to the fluidized bed. The separated biomass is preferably concentrated and removed from the bioreactor via a biomass discharge.

BRIEF DESCRIPTION OF THE DRAWING

Embodiments of this invention will be described with reference to the following Figures, of which.

DETAILED DESCRIPTION OF THE INVENTION

Figure 1:
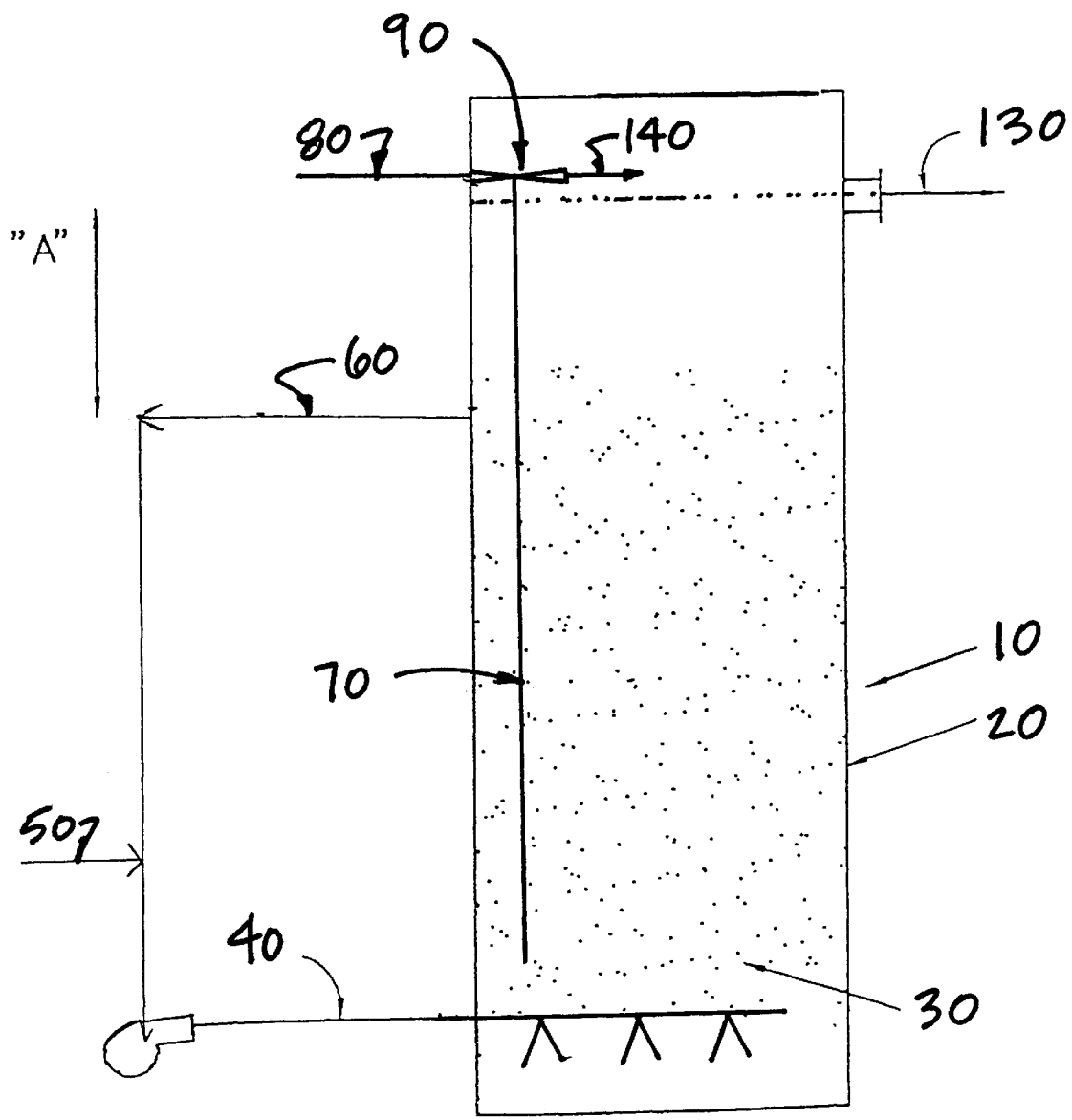
FIG. 1 illustrates an embodiment of a fluidized bed reactor having an adjustable slurry inlet according to aspects of this invention.

Preferred aspects of this invention will now be described with reference to exemplary embodiments selected for illustration in the Figures. It should be appreciated that the scope and spirit of this invention are not limited to the particular embodiments selected for illustration in the Figures, and that the invention is defined separately in the appended claims. It should also be appreciated that the Figures are not rendered to any particular proportion or scale and that any dimensions referred to in the following description are merely exemplary in nature.

Referring generally to the Figures, this invention provides a fluidized-bed reactor 10 including a reaction chamber 20 that is adapted to contain a fluidized bed including a slurry 30 of liquid, media and biomass. The fluidized-bed reactor 10 also includes a lift 70 defining a passage for flow of a portion of the slurry 30. The lift 70 includes a lift inlet such as a lift inlet line 80 for motive fluid, a slurry inlet 170, and slurry discharge at the end of the lift's passage. The motive fluid is introduced into the lift inlet 80 to urge a portion of the slurry 30 through the passage of the lift 70 from the slurry inlet 170 towards the slurry discharge. The height of the slurry inlet 170 is adjustable with respect to the bottom of the reaction chamber.

In operation, and in accordance with a preferred method according to this invention, a biomass discharge 140 is positioned at a height above the height of liquid in the reaction chamber 20. The slurry inlet 170 is positioned at a height above the bottom of the reaction chamber 20. A portion of the slurry 30 is urged from the fluidized bed through the lift's passage. Slurry is discharged through the slurry discharge 140, and the discharged slurry is then returned to the fluidized bed. If a biomass separator 110 is utilized, then biomass is discharged through a biomass discharge 100 connected to the separator 110, and slurry is discharged through a media discharge 210 connected to the separator 110, wherein the slurry has a reduced concentration of biomass relative to the slurry urged to the separator 110 by means of the lift 70.

An ejector is preferably used in order to bring about the flow of the slurry through the lift. Ejectors are frequently cast components having an inlet for a process fluid that is being transported, an inlet for motive fluid that is used to transport the process fluid, and an outlet for the motive fluid and process fluid. As used herein, the term eductor is synonymous with the term ejector. Although eductors and ejectors are referred to throughout this description and are synonymous with each other as used herein, it is recognized that other means can be used for urging the process fluid through the system. Pumps, gravity flow, siphons, impellers, and other mechanical or electromechanical devices can also be used as a means to urge the process fluid from the lift toward the discharge.

Accordingly, media is pumped or otherwise transported from an adjustable elevation within the fluidized bed, flows through a lift (by means of an ejector, for example), and is then returned to the bed in a cleaned condition. In the case of the use of an ejector, the pumping rate and the degree of shear can be controlled by the pressure of motive fluid that is introduced to promote movement of the slurry. Separated biomass flows out of the system with the effluent, or may be concentrated in a separated stream. A hydrocyclone separation operation or a gravity separation operation can be used to perform optional secondary media/biomass separation. Details of exemplary separation devices are described in U.S. Pat. Nos. 5,750,028 and 5,788,842, both of which are incorporated herein by reference.

It has been discovered that a fluidized bed reactor embodying preferred features of this invention confers several significant benefits. For example, the embodiments of the fluidized bed reactor illustrated in the Figures can bring about uninterrupted fluidized bed reactor operation without the need for chemical treatment or moving parts. Also, the illustrated fluidized bed reactor embodiments can help to reduce the depletion of biomass inventory and viability, which can take days or even weeks to restore. By controlling the removal of biomass in accumulated suspended solids from the fluidized bed in accordance with this invention, steady state operation and consistent performance can be achieved.

Preferred aspects of this invention also confer additional benefits. The shear intensity can be adjusted (e.g., by varying the motive fluid pressure) or operated cyclically (e.g., in an on/off time cycle), thereby allowing further optimization for particular applications. A fluidized bed reactor according to preferred aspects of this invention can also be incorporated into an automated control system that causes operation of the device in response to bed height, rate increase in bed height, or based on other control schemes.

Preferred features of this invention will now be described with reference to the embodiments illustrated in individual Figures.

As shown in FIG. 1, a typical fluidized bed comprises a slurry 30 including liquid, a growth media or packing material (such as carbon granules, for example), and biomass. Many suitable forms of media are known in the art. The media is supplied (or inoculated) with microorganisms such as Pseudomonas, Actinomyces, or other bacteria, fungi or molds, for example, which can degrade contaminants carried by the liquid introduced through the feed line 50. Upon passing into contact with the microorganisms, contaminants within the contaminated liquid are degraded. Degradation of the contaminant occurs by the usual mechanism of the particular microorganisms employed.

As the quantity of biomass increases during the bioreaction process, it becomes beneficial to remove some of the biomass that can be considered excess to the bioreaction system. In most instances, the excess biomass includes dead cell mass and residual nutrients and carrier fluid. Frequently, no special disposal procedures or apparatus is required, and the excess biomass typically exits the bioreactor with the effluent 130 and is removed in a settling tank (not shown).

Additionally, the slurry is often subjected to shear in the bioreactor. Shear has two fundamental components: (1) shear stress which is the force per unit area acting on a media particle, and (2) shear rate which is a measure of how the velocity of the fluid changes as distance from the surface of the media increases. Shear can be visualized as liquid flow lines moving at different speeds and directions over the media particles and attached biomass. Such velocity fluctuations occur in turbulent eddies induced by the motive fluid, as described above. The smaller the eddy and the greater the velocity fluctuation, then the greater will be the level of shear and, therefore, the greater the amount of biomass that should be removed from the media particles.

However, such turbulence is sometimes insufficient to remove a desirable quantity of filamentous microorganisms from the media particles. Furthermore, the shear present in typical bioreactors affects the uppermost zones more than the lowermost zones of the bioreactor. Therefore, filamentous microorganisms, which are typically concentrated towards the bottom of the bioreactor, are often unaffected by the shear imparted in the upper zones of the bioreactor. Accordingly, the filamentous microorganisms tend to accumulate in the lowermost portions of the bioreactor (typically the lowermost 33%), thereby causing undesirable bed expansion if the filamentous microorganism growth is not controlled. Other conditions such as elevated oxygen concentration in the lowermost zones of the bioreactor may also promote accumulation in the lowermost portion of the bioreactor.

Specifically, filamentous microorganisms grow in intertwined, thread-like biological growths. This type of growth is characteristic of some species of bacteria, fungi and algae, and such growths can reduce sludge settle-ability and dewater-ability. Additionally, these bacterial, fungal, and algal species may also interfere with drainage of effluent through filters as well as cause the formation of inorganic precipitates on the bottom of the fluidized-bed bioreactor which eventually must be removed. Furthermore, because these microorganisms typically grow in oxygen deficient zones located toward the bottom of the bioreactor, it is difficult to remove the microorganisms from the fluidized-bed bioreactor without affecting the remainder of the bioreactor.

Additionally, the application of shear induced by the fluid pumped into the bottom of the bioreactor is often insufficient to remove the filamentous microorganisms from the media particles and force the filamentous microorganisms to the top of the bioreactor where the filamentous microorganisms can be more easily removed. Therefore, undesirable fluidized-bed expansion can occur in the lowermost regions of bioreactors, even with a recycle line 60 present.

Figure 3:
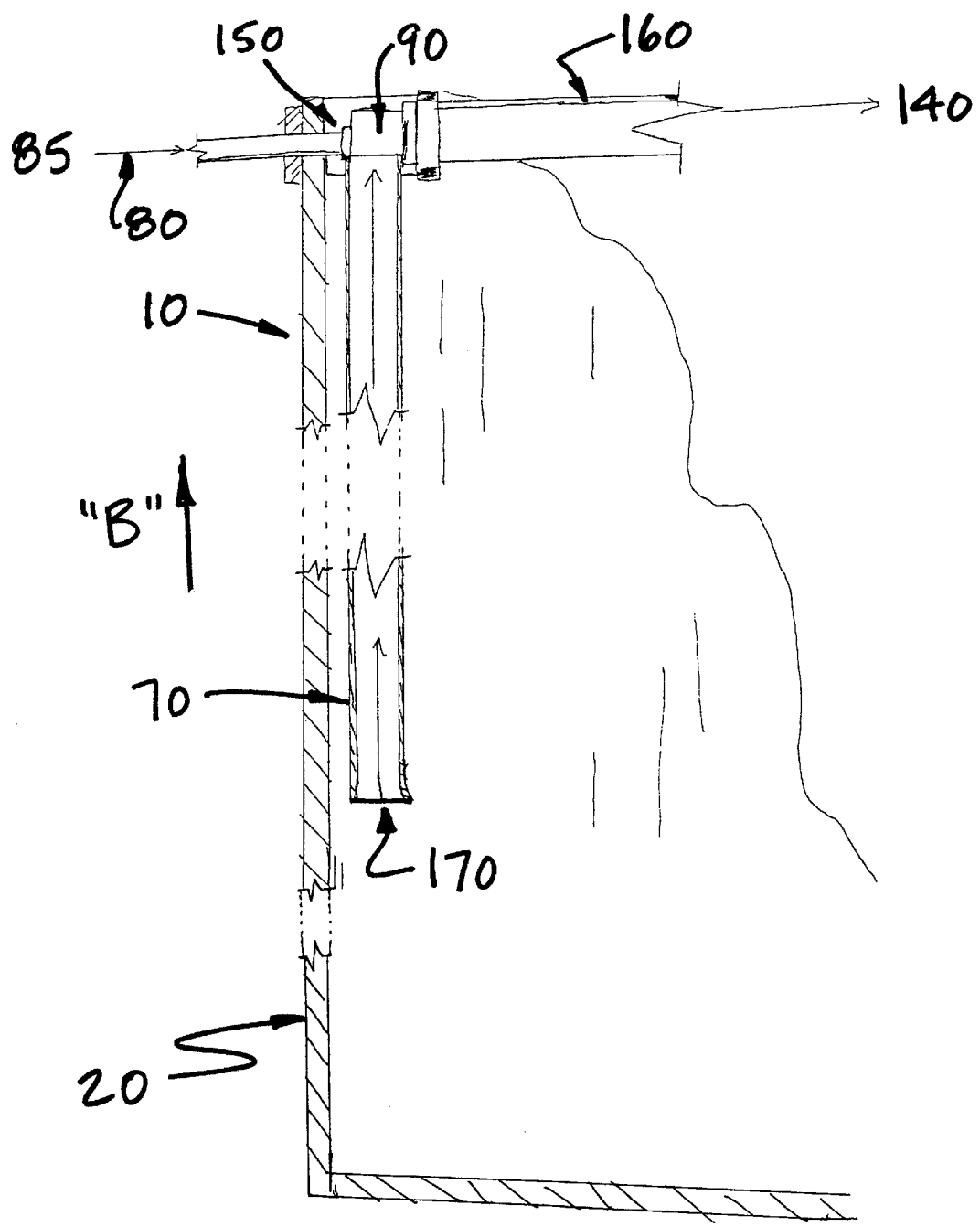
FIG. 3 illustrates a portion of the reactor shown in FIG. 1.

To overcome the problem of fluidized-bed expansion, the height of a slurry inlet 170 is adjustable with respect to the bottom of reaction chamber 20. As shown in FIG. 3, a portion of slurry 30 enters slurry inlet 170 of lift 70 and moves from within the bioreactor up the passage defined by lift 70 in the direction "B" to the top of bioreactor 10 and to the ejector or eductor 90 and subsequently to the slurry discharge 160, where controlled amounts of shear may be imparted on the slurry in the manner described below. An example of an eductor that is suitable for use with a system and method according to this invention is an eductor having a 1¼ inch feed, a 2 inch suction, and a 2 inch discharge, although other urging means can be substituted.

Lift 7 also has a lift inlet 150 for motive fluid 85 provided from lift a inlet line 80. Motive fluid 85 may be a gas or liquid, and is preferably a liquid such as water. Most preferably, motive fluid 85 is a recycled portion of the slurry, as described in more detail below.

Although slurry inlet 170 can be positioned at any height within bioreactor 10 with respect to the bottom of the bioreactor, for the reasons specified below it is preferable to position slurry inlet 170 in the oxygen deficient zone after equilibrium is reached in the fluidized-bed to prevent undesirable buildup of filamentous microorganisms. The elevation of the slurry inlet 170 and/or the eductor 90 is preferably adjustable during operation of the reactor. Such adjustability makes it possible to help establish an equilibrium operation state within the reactor and to optimize the position of the inlet and/or eductor after an equilibrium operation state has been established.

The present invention permits the lifting of a portion of slurry 30, and preferably a portion of slurry 30 located near the bottom of reaction chamber 20, to the top of bioreactor 10. The preferred adjustability of the inlet optimizes this function. In other words, because the height of slurry inlet 170 is adjustable with respect to the bottom of reaction chamber 20, an operator can select slurry from a predetermined elevation within reaction chamber 20. In particular, when slurry inlet 170 is positioned within a zone where shear resistant microbial growth or precipitate occurs and slurry from that zone is removed via lift 70, the size of the zone can be controlled, and accordingly the amount of filamentous microorganisms or precipitates is also controlled. More particularly, because slurry from the zone is removed from reaction chamber 20 and returned to the top of bioreactor 10, where multiple shear forces may be imparted on the slurry, as described below, and because the slurry is subsequently exposed to different conditions at the top of the bioreactor, the formation of filamentous microorganisms in the bioreactor can be reduced and/or controlled.

As described above, previous attempts to impart shear forces on the slurry located in the lower elevations of the bioreactor have met with limited success. However, according to preferred aspects of the present invention, motive fluid 85 is introduced via lift inlet line 80. Although motive fluid 85 is used to lift the slurry, motive fluid 85 has been discovered to create a controlled turbulence which imparts shear forces on the slurry, thereby loosening and removing a portion of the biomass from the media particles present in the slurry. After an amount of shear is imparted on the slurry, the slurry is typically returned through a slurry discharge 160 to reaction chamber 20 as a discharge slurry 140, typically under the force of gravity or pumping action, where the discharged slurry then resettles in the bioreactor. Additionally, while settling, the discharged slurry may be subjected to additional shear forces present in the top zones of the bioreactor, as described above, thereby further enhancing the degree of removal of filamentous microorganisms from the media particles. Excess biomass, water and a portion of the media may be removed from bioreactor 10 with effluent 130.

When introduced in gaseous form, motive fluid 85 creates bubbles that urge slurry 30 in slugs upwardly through lift 70 in the general direction labeled "B" (especially when the motive fluid is introduced at a location along the length or near or at the bottom of the lift 70 as opposed to its top).

Preferably, however, motive fluid 85 is introduced in liquid form and urges the slurry upwardly by pressure differential. In either case, motive fluid 85 is preferably introduced at a controlled rate and in a controlled frequency. In particular, it has been discovered that the shear intensity imparted by motive fluid 85 on slurry 30 may be adjusted by selectively controlling motive fluid 85 pressure, flow volume, fluctuation, and/or force. Additionally, motive fluid 85 may be introduced in a cyclical timing pattern, with on and off cycle times, thereby permitting optimization of the current invention for particular applications.

It is because shear forces are imparted on the portion of the slurry 30 that contains the shear resistant microbial growth or precipitate as well as the regulated rate of removal of the filamentous growth or precipitate that the settling characteristics for the treated waste stream are enhanced (as the growth of the filamentous microorganisms is inhibited). Additionally, the formation of inorganic precipitates within reaction chamber 20 is thereby reduced, which in turn reduces the frequency and duration of down time for cleaning of bioreactor 10. Furthermore, by controlling the removal of biomass and accumulated solids from within the fluidized-bed, the steady state operation of the reactor is more easily maintained.

Figure 2:
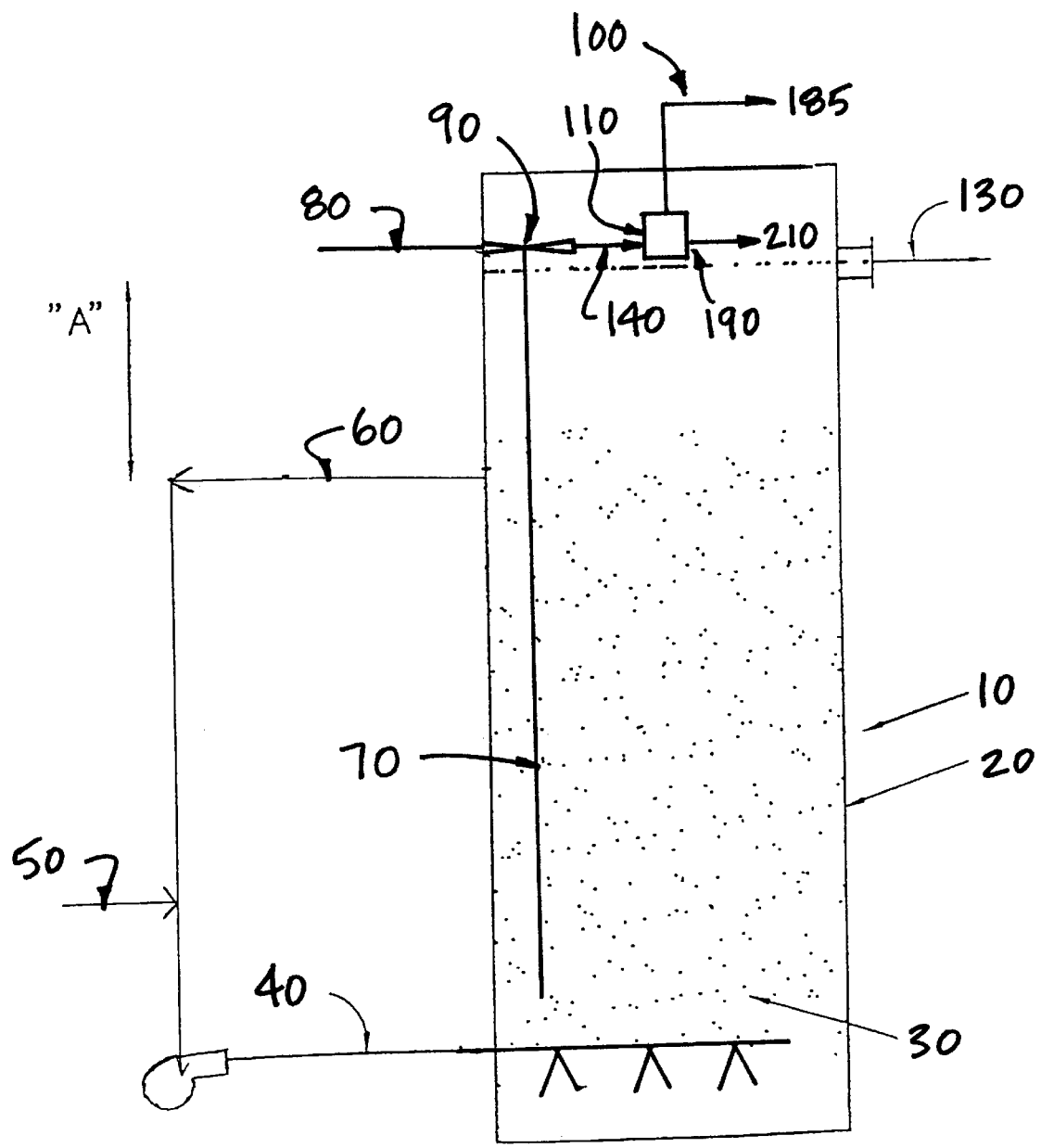
FIG. 2 illustrates another embodiment of a fluidized bed reactor having an optional biomass separator according to aspects of this invention.

An alternative embodiment of this invention illustrated in FIG. 2 removes excess biomass from slurry 30 by providing a biomass separator 110. Although biomass separator 110 may optionally be positioned outside of reaction chamber 20, biomass separator 110 may also be positioned within reaction chamber 20 as shown in FIG. 2. Whether biomass separator 110 is positioned outside reaction chamber 20 or positioned within reaction chamber 20 depends upon design choices and the specific application with which bioreactor 10 is used. Such design choices are within the ability of a skilled artisan in the relevant art.

In this alternative embodiment, and as shown in FIG. 2, biomass separator 110 is connected to ejector 90 adjacent to or within reaction chamber 20 for receiving all or a portion of the ejected slurry 140. Specifically, biomass separator 110 separates a portion of the biomass from the media and water discharged from ejector 90. The biomass may then be concentrated and discharged via a biomass discharge 100, which is connected adjacent to biomass separator 110 for removal of concentrated biomass 185 (as well as some attendant water and media) from reaction chamber 20. Additionally, a slurry discharge 190 is also connected to biomass separator 110. Slurry discharge 190 returns a portion of the media, water and biomass as discharged slurry 210 to the top of the reaction chamber 20 in the same manner as described above.

Figure 4:
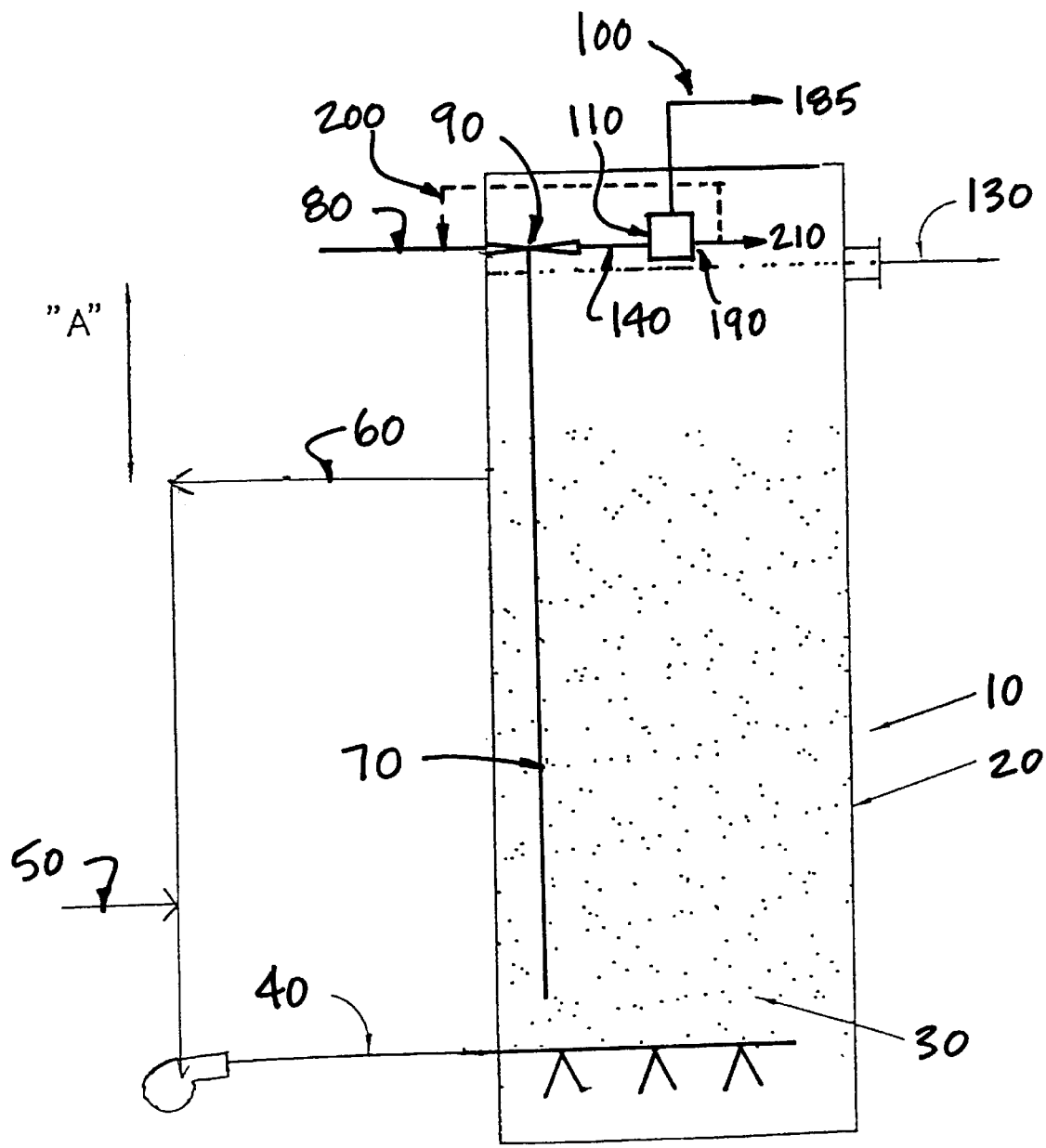
FIG. 4 illustrates still another embodiment of a fluidized bed reactor having an optional slurry recycle according to aspects of this invention.

In an alternative and preferred embodiment illustrated in FIG. 4, biomass separator 110 is connected to a slurry recycle line 200. Slurry recycle line 200 is connected to lift inlet line 80 or lift inlet 150 or directly to the ejector 90. For purposes of connecting slurry recycle line 200 only, lift inlet line 80 and lift inlet 150 are substantially equivalent. By connecting slurry recycle line 200 to lift inlet line 80 or lift inlet 150, all or a portion of discharged slurry 210 may be used as motive fluid 85 to lift the slurry from the applicable zone (or other zone) of the bioreactor to ejector 90 and separator 110, while any remaining portion of discharged slurry 210 is returned to the bioreactor in the manner described above.

Using a portion of discharged slurry 210 as motive fluid provides the advantages of decreasing the operational costs associated with the bioreactor because less outside supplied motive fluid is required. Additionally, by recycling a portion of discharged slurry 210 as motive fluid 85, it has been discovered that the concentration of biomass 185 removed from bioreactor 10 is enhanced. Furthermore, by recycling a portion of discharged slurry 210 as motive fluid, it has been discovered that the amount of media inadvertently removed from the bioreactor with biomass discharge 185 is significantly reduced.

Figure 5:
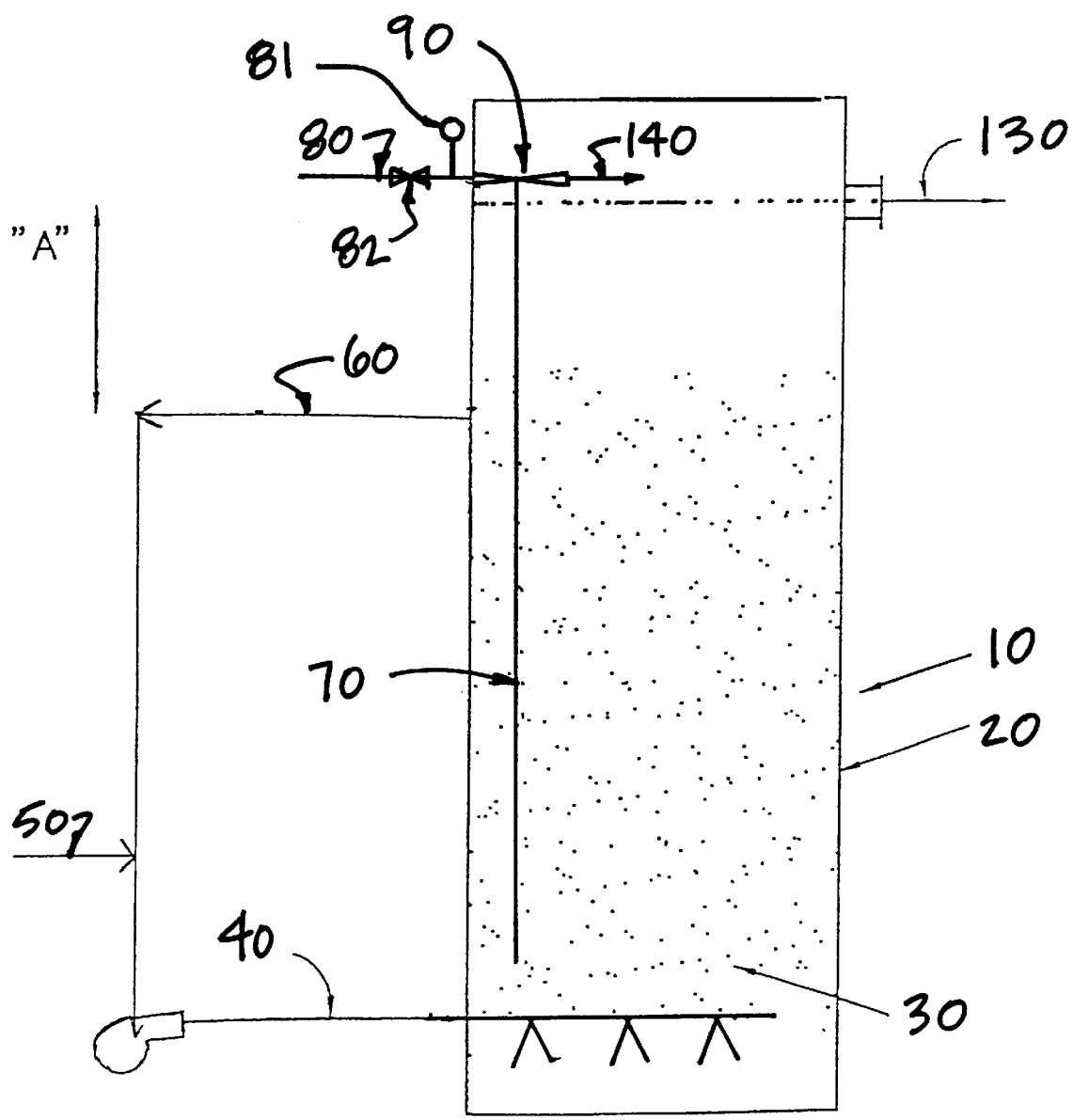
FIG. 5 illustrates yet another embodiment of a fluidized bed reactor having an adjustable motive fluid pressure according to aspects of this invention.

FIG. 5 illustrates yet another preferred embodiment of a fluidized bed reactor according to preferred aspects of this invention. The fluidized bed reactor illustrated in FIG. 5 is the same as that illustrated in FIG. 1, except that the reactor illustrated in FIG. 5 also includes an optional means for adjusting the inlet pressure of motive fluid. More specifically, a means such as a pressure indicator 81 is provided along the lift inlet line 80 preferably just upstream of the ejector 90. The pressure indicator 81 is connected to the lift inlet line 80 in order to indicate the pressure of motive fluid as it is delivered to the inlet of the ejector 90.

A pressure control valve 82 is also provided along the lift inlet line 80, preferably upstream of the pressure indicator 81, in order to control the pressure of motive fluid as it is delivered to the inlet of the ejector 90. In this manner, the pressure of the motive fluid can be adjusted so that the rate of flow delivered to the lift 70 and/or ejector 90 can be controlled. More specifically, as the pressure or rate of motive fluid delivered into the ejector 90 is adjusted, the rate of flow of slurry through the passage of lift 70 into the ejector 90 is likewise controlled. In this manner, the rate at which slurry is withdrawn from the fluidized bed, and the degree of shear imparted, can be controlled in order to maintain an optimized equilibrium of the fluidized bed.

Figure 6:
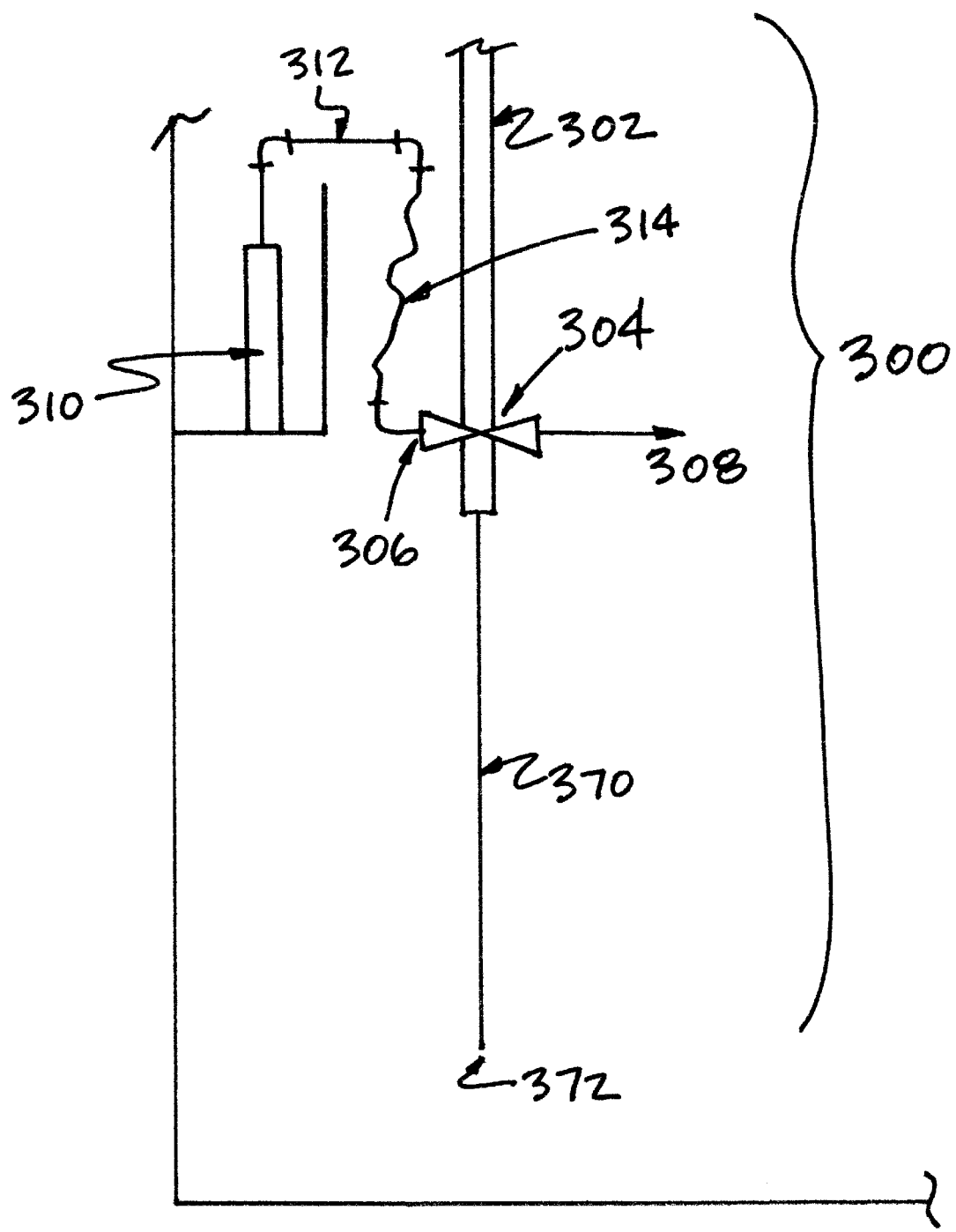
FIG. 6 illustrates a portion of an adjustable slurry inlet adapted for use in a reactor according to aspects of this invention.

FIG. 6 is provided to illustrate a preferred system 300 for providing an adjustable lift, wherein the elevation of the lift inlet and/or the ejector can be changed during operation of the bioreactor in order to optimize its performance and efficiency. Specifically, system 300 includes a lift support 302 on which the eductor or ejector 304 is mounted. The lift support 302 can be secured to or be a structural component of the reaction chamber 20 such as a handrail, for example. The eductor 304 has an eductor inlet 306 for receiving motive fluid and an open eductor discharge 308 for returning slurry to the fluidized bed or delivering the slurry to a separator. A lift 370 having a slurry inlet 372 is also connected to the eductor 304 to deliver slurry from the fluidized bed to the eductor or ejector 304. The lift can be formed from a tube, a pipe, a conduit, or any other means for providing a flow passageway. For example, in one preferred embodiment, the lift is formed from 2 inch, schedule 80 PVC pipe. Other materials can, of course, be selected based on design constraints.

To help facilitate the adjustability of the elevation of the slurry inlet 372 of the lift 370 and/or the eductor 304, motive fluid can be delivered to the inlet 306 of the eductor 304, from a source 310 of motive fluid, by means of a delivery pipe 312 and a flexible delivery hose 314. It will be understood that a flexible delivery hose 314, or an equivalent means for maintaining a fluid flow connection between two components that move with respect to one another, is preferred in order to accommodate the adjustable height of the lift 370 and/or the eductor 304 as it is moved vertically along the lift support 302. The connection can be formed by a coiled hose, a flexible conduit, a tube, a pipe, a channel, or any other structure capable of forming a passageway. For example, 1½ inch hose can be used to form a connection between a source of motive fluid and the eductor. Other means can be substituted therefor.

The structure shown in FIG. 6 is an example of a means for adjusting the elevation of the suction inlet and/or discharge. In the illustrated embodiment, the elevations are adjustable by changing the length of the suction pipe and/or the eductor's elevation. Until equilibrium is established within the reactor chamber, and at the outset of using the reactor chamber, a starting elevation for the suction and discharge is selected. For example, a starting point for the elevation of the suction inlet might be about two (2) feet from the bottom of the reaction chamber, and a starting elevation of the discharge port might be about ten (10) feet from the bottom.

Although illustrated and described herein with reference to certain specific embodiments, the present invention is nevertheless not intended to be limited to the details shown and described. Rather, the claims should be read to include various modifications within the scope and range of equivalents of the claims, without departing from the spirit of the invention.

What is claimed:

1. A fluidized-bed bioreactor comprising:
   a reaction chamber adapted to contain a fluidized bed comprising a slurry of liquid, media and biomass;
   a lift defining a passage for flow of a portion of said slurry, said lift comprising a lift inlet for motive fluid, a slurry inlet, and a slurry discharge, wherein motive fluid is introduced into said lift through said lift inlet to urge said portion of said slurry through said passage of said lift from said slurry inlet toward said slurry discharge;
   wherein the height of said slurry inlet is adjustable with respect to the bottom of said reaction chamber.

2. The bioreactor of claim 1, wherein said lift inlet is connected for flow of media from a lower most portion of said fluidized bed.

3. The bioreactor of claim 1, wherein said lift inlet for motive fluid comprises a liquid inlet for introducing motive liquid, thereby producing pressure to urge said portion of said slurry through said lift.

4. A fluidized-bed bioreactor comprising:
   a reaction chamber adapted to contain a fluidized bed comprising a slurry of liquid, media and biomass;
   a lift connected adjacent to a separator for flow of a portion of said slurry, said lift comprising a lift inlet for motive fluid, wherein motive fluid is introduced into said lift through said lift inlet to urge said portion of said media through said lift;
   said separator connected to said reaction chamber for receiving a portion of said media from said fluidized bed, a biomass discharge connected adjacent to said separator for flow of biomass from said portion of said slurry urged through said lift;
   a slurry discharge connected adjacent to said separator for flow of slurry from said portion of said slurry urged through said lift;
   wherein the height of said slurry inlet is adjustable with respect to the bottom of said reaction chamber.

5. The bioreactor of claim 4, wherein said lift inlet is connected for flow of media from a lower most portion of said fluidized bed.

6. The bioreactor of claim 4, wherein said lift inlet for motive fluid comprises a fluid inlet for introducing motive gas, thereby producing gas bubbles to urge said portion of said slurry through said lift.

7. The bioreactor of claim 4, further comprising a slurry recycle connected to said slurry discharge and is also connected to said lift inlet.

8. A method for cleaning a bioreactor comprising a reaction chamber adapted to contain a fluidized bed comprising a slurry of liquid, media and biomass, a lift, wherein said lift comprises a passage for flow of a portion of said slurry, said lift comprising a lift inlet for motive fluid, a height adjustable slurry inlet, and a slurry discharge, the steps comprising:
   (a) positioning said biomass discharge at a height above the height of liquid in said reaction chamber;
   (b) positioning said slurry inlet at a height above the bottom of said reaction chamber;
   (c) urging a portion of said slurry from said fluidized bed through said passage;
   (d) discharging said slurry through said slurry discharge;
   (e) returning said slurry discharged through said slurry discharge, to said fluidized bed.

9. The method of claim 8, wherein said bioreactor further comprises a separator connected adjacent to said reaction chamber for receiving a portion of said slurry from said fluidized bed, a biomass discharge connected adjacent to said separator for flow of biomass from said portion of said slurry urged through said lift and a slurry discharge connected to said lift for flow of slurry urged through said lift, the steps further comprising:
   (f) discharging biomass through said biomass discharge from said slurry urged through said lift.
   (g) discharging slurry through said media discharge from said slurry urged through said lift; wherein said slurry has a reduced concentration of biomass relative to said slurry urged through said lift.

10. The method of claim 9, wherein said urging comprises introducing into said lift a motive fluid.

11. The method of claim 9, wherein said urging step comprises urging a portion of said slurry from a lowermost portion of said fluidized bed.

12. The method of claim 9 wherein slurry discharged through said slurry discharge is returned under the force of gravity to said fluidized bed.

13. The method of claim 9 wherein slurry discharged through said slurry discharge is returned by pumping to said fluidized bed.

14. The method of claim 9 wherein a portion of said slurry discharged through said slurry discharge is returned to said lift inlet.

15. A fluidized-bed bioreactor comprising:
   a reaction chamber adapted to contain a fluidized bed comprising a slurry of liquid, media and biomass;
   a lift defining a passage for flow of a portion of said slurry, said lift comprising a lift inlet for motive fluid, a slurry inlet, and a slurry discharge, wherein motive fluid is introduced into said lift through said lift inlet to urge said portion of said slurry through said passage of said lift from said slurry inlet toward said slurry discharge; and
   means for adjusting the shear applied to the slurry by the motive fluid.

16. The bioreactor of claim 15, said means for adjusting the shear applied to the slurry by the motive fluid comprising a valve connected to control the flow of motive fluid toward said lift.

17. A fluidized-bed bioreactor comprising:
   a reaction chamber adapted to contain a fluidized bed comprising a slurry of liquid, media and biomass;
   a lift defining a passage for flow of a portion of said slurry, said lift comprising a lift inlet for motive fluid, a slurry inlet, and a slurry discharge, wherein motive fluid is introduced into said lift through said lift inlet to urge said portion of said slurry through said passage of said lift from said slurry inlet toward said slurry discharge; and a passageway connected to deliver at least a portion of slurry from said slurry discharge toward said lift inlet to provide or supplement the motive fluid.

18. A fluidized-bed bioreactor comprising:

a reaction chamber adapted to contain a fluidized bed comprising a slurry of liquid, media and biomass, said fluidized bed having a lower portion including filamentous organisms, a central portion above said lower portion including oxygenated slurry, and an upper portion including oxygenated water;

a lift defining a passage for flow of a portion of said slurry, said lift comprising a lift inlet for motive fluid, a slurry inlet, and a slurry discharge, wherein motive fluid is introduced into said lift through said lift inlet to urge said portion of said slurry through said passage of said lift from said slurry inlet toward said slurry discharge;

wherein the height of said slurry inlet is adjustable with respect to the bottom of said reaction chamber, and said slurry inlet is adjusted to remain within said lower region of said fluidized bed.

* * * * *